US012594184B2

(12) United States Patent
Su et al.

(10) Patent No.: US 12,594,184 B2
(45) Date of Patent: Apr. 7, 2026

(54) PACKAGED LUBRICATED CONDOM

(71) Applicant: RECKITT BENCKISER HEALTH LIMITED, Berkshire (GB)

(72) Inventors: Qun Su, Qingdao (CN); Zhiyuan Wang, Qingdao (CN); Xufeng Wu, Shanghai (CN)

(73) Assignee: Reckitt Benckiser Health Limited (GB)

( * ) Notice: Subject to any disclaimer, the term of this patent is extended or adjusted under 35 U.S.C. 154(b) by 160 days.

(21) Appl. No.: 18/264,444

(22) PCT Filed: Feb. 10, 2022

(86) PCT No.: PCT/GB2022/050361
§ 371 (c)(1),
(2) Date: Aug. 7, 2023

(87) PCT Pub. No.: WO2022/172010
PCT Pub. Date: Aug. 18, 2022

(65) Prior Publication Data
US 2024/0041640 A1     Feb. 8, 2024

Related U.S. Application Data

(63) Continuation of application No. PCT/CN2021/076570, filed on Feb. 10, 2021.

(30) Foreign Application Priority Data

Mar. 30, 2021     (GB) ...................................... 2104507

(51) Int. Cl.
*A61F 6/00*          (2006.01)
*A61F 6/04*          (2006.01)
*A61K 47/26*         (2006.01)

(52) U.S. Cl.
CPC .............. *A61F 6/005* (2013.01); *A61F 6/04* (2013.01); *A61K 47/26* (2013.01)

(58) Field of Classification Search
CPC .... A61F 6/04; A61F 6/065; A61F 6/02; A61F 6/20; A61F 6/00; A61K 47/26; A61K 9/0014; A61K 9/0034; A61K 31/047; A61K 31/70; A61Q 90/00; A61P 17/00
See application file for complete search history.

(56) References Cited

U.S. PATENT DOCUMENTS

| | | | |
|---|---|---|---|
| 5,885,591 A | 3/1999 | Ahmad et al. | |
| 8,770,201 B2 | 7/2014 | Zedalis et al. | |
| 2005/0076917 A1 | 4/2005 | Wray et al. | |
| 2008/0193489 A1* | 8/2008 | De Armond | A61K 31/70 424/400 |
| 2009/0107513 A1* | 4/2009 | Zedalis | A61F 6/04 427/2.3 |
| 2012/0181726 A1* | 7/2012 | Platt | B29C 41/22 264/254 |
| 2014/0193532 A1 | 7/2014 | Ahmad et al. | |
| 2016/0017254 A1* | 1/2016 | Cojocariu | A61K 9/06 508/309 |

FOREIGN PATENT DOCUMENTS

| | | |
|---|---|---|
| CN | 107998461 A | 5/2018 |
| CN | 110279511 A | 9/2019 |
| JP | S497274 B1 | 2/1974 |
| JP | H11021230 A | 1/1999 |
| JP | 2002165822 A | 6/2002 |

OTHER PUBLICATIONS

International Search Report and Written Opinion received in corresponding PCT Application No. PCT/GB2022/050361 mailed May 16, 2022.
Combined Search and Examination Report received in corresponding United Kingdom Application No. GB104507.5 mailed Oct. 1, 2021.

* cited by examiner

*Primary Examiner* — Ophelia A Hawthorne
(74) *Attorney, Agent, or Firm* — Lerner David LLP

(57) ABSTRACT

A packaged condom may include a sealed package and, within the package, a condom including natural rubber latex and/or synthetic polyisoprene. The condom includes an aqueous lubricant on one or more surfaces thereof. The aqueous lubricant is in contact with the natural rubber latex and/or synthetic polyisoprene. The aqueous lubricant includes a thickener and one or more organic compounds in a total amount of from 5 to 25% by weight of the aqueous lubricant, the one or more organic compounds independently selected from a poly-hydric alcohol and a sugar. Each of the one or more organic compounds may have at least 4 hydroxyl groups and a molecular weight of from 120 to 10000.

19 Claims, No Drawings

PACKAGED LUBRICATED CONDOM

CROSS-REFERENCE TO RELATED APPLICATIONS

This application is a U.S. National Phase of International Patent Application No. PCT/GB2022/050361, filed on 10 Feb. 2022, which claims priority to United Kingdom Patent Application No. 2104507.5, filed on 30 Mar. 2021, and International Patent Application No. PCT/CN2021/076570, filed on 10 Feb. 2021. The entire contents of these applications are incorporated herein by reference in their entirety.

BACKGROUND

The present invention relates to a packaged lubricated condom. In particular, the present invention relates to a packaged condom lubricated with an aqueous lubricant, the condom desirably presenting a transparent appearance to the end user.

Personal lubricants are specialised lubricants which serve to reduce friction with body tissues during sexual activity. In particular, personal lubricants may be used to provide lubrication, or slip, during sexual activity by application directly to the vagina. For example, personal lubricants can be used to increase pleasure or reduce pain during sexual intercourse and can aid in reducing vaginal dryness. In medicine, personal lubricants may be employed for gynaecological examinations and the like.

Condoms may be pre-provided with a lubricant on their surface. The technical considerations for such lubricants differ from standalone personal lubricants since the composition must be stable with the condom material (and the condom packaging material) for long storage periods. In addition, the lubricant should not be rubbed off the condom too quickly during sexual activity, and the way the lubricant is dosed onto the condom during manufacturing also affects the requirements, for example in terms of viscosity and tackiness, while still providing the desired degree of lubricity.

Lubricated condoms have been available for many years. The most common lubricants are silicone-based, since silicone lubricants are highly compatible with the long term integrity of common condom materials (including natural rubber latex ("NRL") and synthetic polyisoprene ("PI")) while providing good lubricity. However, in view of their hydrophobicity, silicone lubricants can be difficult to wash off once adhered to the skin or clothes. They are therefore sometimes perceived as messy by consumers.

To solve this problem, various different water soluble lubricants have been tried. However, many of these lubricants, especially when dosed on an NRL or PI condom, cause the appearance of the condom to become more opaque during storage. In more detail, these condoms, prior to the application of the lubricant and any finishing powder, usually have a transparent appearance. A transparent appearance is desirable to consumers, in part because they associate it with thinness. Many of the existing aqueous lubricants have a tendency to whiten the condoms and make them appear opaque, thereby degrading their appearance and making them less desirable in the eyes of consumers. However, the exact mechanism by which this happens is not well understood in the art.

U.S. Pat. No. 6,196,227 B1 recognises the problem of whitening caused by water soluble lubricants when dosed onto condoms. It is postulated in this document that the whitening may be caused by water absorption, and the document teaches that the water content of the lubricant should be limited to prevent the surface of the condom from becoming white. It is also disclosed that humectants, such as glycerine, propylene glycol and polyethylene glycol may be added to aid with wettability and lubricity.

Aside from their tendency to whiten condoms such as NRL and PI condoms, there are also issues with the osmolality of aqueous lubricants. Historically, aqueous standalone personal lubricants have tended to have an osmolality much higher than the typical vaginal osmolality of 200-300 mOsm/kg. It is now appreciated that the osmolality of a lubricant is important because the epithelial cells lining the vaginal wall will constantly try and maintain homeostasis. Hyperosmolar lubricants cause the cells of the vagina to release fluid to dilute the lubricant. This may result in epithelial cell damage, which in turn results in an increased risk of infection due to the compromised epithelial barrier. There may also be increased dryness of the vagina. This is particularly problematic for menopausal females as the use of the hyperosmolar lubricant exacerbates vaginal dryness. In 2012, the World Health Organisation (WHO) recommended that healthcare organisations procure standalone personal lubricants which have an osmolality of less than 1200 mOsm/kg. However, formulating a standalone personal lubricant within this range is not straightforward whilst also balancing the need to achieve a number of other parameters including the required viscosity, slip properties, and rheological stability during storage. This is reflected in the fact that many aqueous standalone lubricants on the market today still have an osmolality of 2000-6000 mOsm/kg, despite the WHO recommendations nearly a decade ago. It is even more challenging to try to apply these WHO recommendations to condom lubricants, for which an additional set of technical constraints apply. Furthermore, since the typical quantity of lubricant pre-applied to the condom is much less than the quantity of a standalone lubricant manually applied by the consumer, it has not been seen in the art as so essential to meet this osmolality criteria for lubricated condoms, potentially at the expense of other important properties.

The osmolality of a solution in Osm/kg is defined as the number of osmoles of solute per kilogram of solvent. The osmolalities of the aqueous lubricants disclosed in U.S. Pat. No. 6,196,227 B1, which was published in 2001, will be high in view of their high concentrations of low molecular weight solute molecules. U.S. Pat. No. 6,196,227 B1 does not, therefore, disclose aqueous lubricants which would correlate with the newer WHO recommendations for osmolality of a standalone personal lubricant. Increasing the water content and decreasing the solute concentration of the lubricants of U.S. Pat. No. 6,196,227 B1 would decrease their osmolality, but would also be expected to give rise to whitening of the condom, if the water absorption effect postulated in this document is followed. It would also be expected to compromise the physical properties of the lubricant, since each of the solutes disclosed in this document is included to maintain a particular property of the lubricant.

There remains a need for low-osmolality aqueous lubricants that have suitable physical properties for use on a condom, particularly one comprising NRL or PI, and have reduced adverse effect on the transparency of the condom during storage.

BRIEF DESCRIPTION OF THE INVENTION

According to a first aspect, the present invention provides a packaged condom comprising:

a sealed package; and within the package, a condom comprising natural rubber latex and/or synthetic polyisoprene;

wherein the condom comprises, on one or more surfaces thereof and in contact with the natural rubber latex and/or synthetic polyisoprene, an aqueous lubricant; and wherein the aqueous lubricant comprises:

a thickener; and in a total amount of from 5 to 25% by weight of the lubricant, one or more organic compounds independently selected from the group consisting of a polyhydric alcohol and a sugar, each of said one or more organic compounds having at least 4 hydroxyl groups and a molecular weight of from 120 to 10000.

The present inventors have found that the inclusion of such a polyhydric alcohol and/or sugar in the specified amount in an aqueous lubricant helps to maintain the transparency and prevent whitening of a natural rubber latex condom during storage, while maintaining a low osmolality. Without wishing to be bound by theory, it is believed that natural rubber latex condoms are particularly susceptible to the whitening effect of aqueous lubricants because of the interaction of water with the impurities or additives in the natural rubber latex. Whilst synthetic polyisoprene has fewer impurities (such as proteins), it still has capacity for whitening. The same principle should apply when NRL/PI is comprised in the condom together with another (preferably also initially transparent) material, provided that the lubricant is not shielded from contact with the NRL/PI by that other material. It is believed that the inclusion of polyhydric alcohols or sugars having a high number of hydroxyl groups (at least 4) in the specified amounts allows the extent of the interaction between the water of the lubricant and the impurities or additives in the condom material to be reduced or eliminated. As a result of the molecular weight of the polyhydric alcohol or sugar, it can be included in a sufficient quantity to have the desired anti-whitening effect, without giving rise to an unacceptably high lubricant osmolality. Advantageously, the aqueous lubricants of the present invention also provide good lubricity and are non-sticky. They are also fully compatible with the condom material and do not impact on the physical properties of the condom, such as burst pressure, burst volume and tensile strength.

According to a second aspect, the present invention provides a method for preparing a packaged condom, the method comprising:

(i) providing an aqueous lubricant, wherein the aqueous lubricant comprises a thickener and, in a total amount of from 5 to 25 wt % by weight of the lubricant, one or more organic compounds independently selected from the group consisting of a polyhydric alcohol and a sugar, each of said one or more organic compound(s) having at least 4 hydroxyl groups and a molecular weight of from 120 to 10000;

(ii) providing a condom as defined in the first aspect;

(iii) applying a dose of the aqueous lubricant to one or more surfaces of the condom to form a lubricated condom in which the lubricant is in contact with the natural rubber latex and/or synthetic polyisoprene; and (iv) sealing the lubricated condom within a package.

According to a third aspect, the present invention provides a packaged condom obtainable by or obtained by the method of the second aspect.

According to a fourth aspect, the present invention provides the use of an aqueous lubricant as defined in the second aspect to lubricate one or more surfaces of a condom as defined in the first aspect, such that the lubricant is in contact with the natural rubber latex and/or synthetic polyisoprene, while maintaining the transparency of the condom during storage within a sealed package.

DETAILED DESCRIPTION OF THE INVENTION

The present invention will now be described further. In the following passages different aspects/embodiments of the invention are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The present invention provides a packaged condom comprising a sealed package and, within the package, a lubricated condom. The sealed package isolates the condom from the external environment, preferably to the extent that molecules within the package do not readily traverse the package boundaries, and oxygen does not readily traverse into the packaging (the low level at which these molecules and oxygen may traverse is within the level accepted in the condom industry). Suitable sealed packages for condoms are known in the art and may include, for instance, two sheets of a laminate material sealed along their edges around the condom. The laminate material may, for instance, include a layer of aluminium. Another possible sealed package is a plastic pot sealed with a film lid, or so-called "butter dish". The condom is preferably provided within the package in a rolled state. The condom is preferably a male condom, preferably one intended to cover substantially the entire penis.

The condom comprises natural rubber latex ("NRL") and/or synthetic polyisoprene ("PI"). Optionally, the NRL and/or PI is present in a blend with one or more other polymeric condom materials, which may be an elastomer (e.g. polyurethane, "PU"). Alternatively or in addition, the NRL and/or PI may be provided in one or more external layers of the condom (whether the penis-facing side or the opposite side), provided that it comes into contact with the lubricant. Preferably, however, NRL and/or PI is the only elastomer or the only polymeric condom material in the condom. Preferably, the condom is a natural rubber latex condom. That is, the condom is formed from natural rubber latex or a natural rubber latex base compounded with one or more additives. Natural rubber latex typically comprises cis-1,4-polyisoprene together with small amounts of impurities, such as proteins, fatty acids, inorganic salts and the like. Synthetic polyisoprene does not contain e.g. the allergenic proteins found in natural rubber latex. Suitable formulations of natural rubber latex and synthetic polyisoprene are known in the art.

The condom itself may be manufactured in any suitable way. Typically, this is done by dipping a condom-shaped former into a latex or latex blend to form a film which is subsequently dried and cured. It will be understood that the manufacture of suitable rubber latexes, and the subsequent formation of condoms therefrom, are well understood procedures to those skilled in the art. As explained above, the present inventors believe that NRL and PI condoms are particularly susceptible to the opacifying effect of aqueous lubricants. NRL and PI condoms, when provided in a dry state and before being coated with lubricant or finishing powder, are usually transparent and essentially colourless (though some may naturally have a slight yellow tinge). It will be appreciated that this is not always the case. Occasionally, for instance, opacifiers or colourants may be included in the latex formulation where an opaque or coloured condom is desired. However, there is a growing consumer desire for transparent condoms, in part because they enhance the perception of thinness, which is again an increasingly desirable trait in a condom in many markets.

Preferably, the condom of the present invention is formed from a transparent material. That is, the condom, prior to the application of the aqueous lubricant or any optional finishing powder, is transparent. The problem of reduction in transparency is particularly acute for condoms which are transparent prior to lubrication, since the effect caused by a typical aqueous lubricant is far more visible than if the condom were already substantially opaque. Accordingly, the advantageous effect of the aqueous lubricant used in the invention is particularly noticeable for condoms which are transparent to start with.

The condom may be transparent and coloured, or transparent and colourless or essentially colourless. It will be understood that discussions of "whitening" herein apply equally to opacifying of coloured condoms. Preferably, the formulation of the condom includes no added colouring agents; consumers may be tolerant of more opacity when the condom is already designed to be coloured.

By "transparent" it is meant the property of transmitting visible light without appreciable scattering such that an object lying beyond the condom can be seen through the condom. It is to be understood that the term "transparent", as used herein, encompasses materials which scatter a limited amount of light but not those which are substantially opaque and do not transmit an appreciable amount of light. Many natural rubber latex condoms have a yellowish tinge to them, resulting from some limited scattering of light, while still being largely see-through. Such condoms are considered "transparent" for the purposes of the present invention. When the condom is packaged in a rolled form, it is to be understood that the property of transparency refers to the condom in its unrolled state, since the rolled portion of a rolled condom can appear to be substantially opaque, even if the condom material itself is transparent.

The condom of the present invention is preferably formed from a material having a haze value of at most 70%. That is, the condom, prior to the application of the aqueous lubricant or any optional finishing powder, preferably has a haze value of at most 70%. More preferably, the haze value is at most 60%, still more preferably at most 50%, still more preferably at most 40%, and most preferably at most 30%. In some embodiments, the haze value is at least 10%, or at least 15%. In embodiments including a finishing powder, the condom preferably also has a haze value lying within these ranges after the application of the finishing powder but before the application of the lubricant. The haze value of a sample can be measured using a UV-Visible spectrophotometer and quantifies the proportion of incident light that is scattered as it passes through the sample. The lower the haze value, the more transparent the material. In the context of the present disclosure, the haze value is defined in accordance with ASTM Standard D 1003-00 and refers to the percentage of light which, in passing through the material, deviates from the incident beam at an angle of greater than 2.5 degrees from the normal (Wide Angle Scattering). Preferably, the haze value is a mean of three measurements taken at an open end, closed end, and midpoint along a length of the condom in its unrolled rate. Preferably, the haze value is determined in accordance with the method disclosed in the Examples.

The invention encompasses condoms which have a pattern or other surface features applied to one or more surfaces thereof, for example ribs or dots intended to provide physical stimulation to the user or their partner. However, in an embodiment, the condom is free of any surface indentations or protrusions which are visible to the human eye. The advantageous effect on transparency is more likely to be noticeable in a condom with a surface lacking raised surface features, which may themselves scatter light.

In embodiments of the invention, the condom has a thickness of 60 microns or less; 55 microns or less; 50 microns or less; 45 microns or less; 40 microns or less; and/or at least 20 microns; at least 25 microns; or at least 30 microns. The thinner the condom, the greater the expectation for transparency from the consumer, but the condom should also maintain sufficient structural integrity to perform its primary function as a barrier.

The condom of the present invention comprises, on one or more surfaces thereof, an aqueous lubricant. The one or more surfaces may be an inner surface and/or an outer surface of the condom. "Inner" in the context of a male condom refers to the penis-facing side, whereas "outer" refers to the side facing the user's partner. Preferably, the aqueous lubricant is present on at least the outer surface of the condom. Preferably, said one or more surfaces are substantially coated with the lubricant. Preferably, at least 25% by area of said one or more surfaces are coated with the lubricant, more preferably at least 40%, still more preferably at least 60% and most preferably at least 70%. It is to be understood that the condom has, in an unrolled state, a length extending from an open end to a closed end of the condom. Said one or more surfaces are preferably coated along at least 25% of said length, more preferably at least 50% of said length, more preferably at least 60%, still more preferably at least 70% and most preferably at least 80%. Preferably, the lubricant is comprised on the one or more surfaces of the condom in an amount of from 100 mg to 1.5 g, more preferably from 200 mg to 1 g, still more preferably from 300 to 800 mg, and most preferably from 400 to 700 mg.

The lubricant comprises one or more organic compounds independently selected from the group consisting of a polyhydric alcohol and a sugar, each of which must have at least 4 hydroxyl groups and a molecular weight of from 120 to 10000. The total amount of these organic compound(s) is from 5 to 25 wt %. As explained above, it is believed that the inclusion of polyhydric alcohols and/or sugars having a high number of hydroxyl groups (at least 4) in the specified amount allows the interaction between the water of the lubricant and the impurities/additives in the surface of the natural rubber latex and/or PI to be reduced or eliminated, thereby maintaining the transparency of the condom and preventing the whitening associated with other aqueous lubricants on such condoms. As a result of the molecular weight of the polyhydric alcohol and/or sugar, it can be included in a sufficient quantity to have the desired anti-whitening effect, without giving rise to an undesirably high lubricant osmolality.

In embodiments of the invention, the total amount of these specified organic compound(s) in the lubricant is:

24 wt % or less; 23 wt % or less; 22 wt % or less; 21 wt % or less; 20 wt % or less; 19 wt % or less; 18 wt % or less; 17 wt % or less; 16 wt % or less; 15 wt % or less; 14 wt % or less; 13 wt % or less; 12 wt % or less; 11 wt % or less; or 10 wt % or less;

and/or 6 wt % or more; 7 wt % or more; 8 wt % or more; 9 wt % or more; 10 wt % or more; 11 wt % or more; or 12 wt % or more.

For example, the lubricant may comprise a total amount of from 5 to 24 wt % of these organic compound(s) by weight of the lubricant, or from 5 to 23 wt %, or from 5 to 22 wt %, or from 5 to 21 wt %, or from 5 to 20 wt %, or from 5 to 19 wt %, or from 5 to 18 wt %, or from 7 to 15 wt %.

The term polyhydric alcohol refers to an alcohol having at least 2 hydroxyl groups. As noted above, however, the polyhydric alcohol(s) used in the present invention have at least 4 hydroxyl groups. The polyhydric alcohol(s) used in the present invention may include polyhydric alcohol derivatives such as ethers and esters, provided the number of free hydroxyl groups is at least 4. In some embodiments, however, the polyhydric alcohol does not contain any functional groups other than hydroxyl groups. In other embodiments, the polyhydric alcohol consists of carbon, hydrogen and oxygen atoms. Preferably, the polyhydric alcohol is water-soluble. Preferably, the polyhydric alcohol is present in the lubricant in a fully dissolved state at a temperature of 25° C., preferably at least throughout the range of 10 to 35° C. This ensures that the polyhydric alcohol does not, itself, scatter light and contribute to an increase in opacity of the lubricated condom.

The term sugar, as used herein, refers to a water-soluble monosaccharide, disaccharide, oligosaccharide or polysaccharide. By water-soluble, it is meant that the sugar dissolves in water at a temperature of 25° C. Examples of suitable monosaccharides include glucose, galactose, ribose, deoxyribose, L-arabinose, fructose, sorbose and xylose. Examples of suitable disaccharides include sucrose, trehalose, lactose and maltose. Examples of suitable polysaccharides include glycogen. The term sugar, as used herein, encompasses sugar derivatives such as ethers and esters of monosaccharides, disaccharides, oligosaccharides or polysaccharides. Preferably, however, the sugar does not contain any functional groups other than the hydroxyl groups on the carbon atoms of the one or more rings of the sugar, the in-ring oxygen atom(s) and any acetal linkages. It will be appreciated that this statement refers to the ring form of the sugar. The ring form of the sugar may exist in equilibrium with an open chain form in aqueous solution. The open chain form will include a carbonyl group. In cases where the sugar exists in equilibrium with an open chain form, references herein to the number of hydroxyl groups in the compound refers to the number of hydroxyl groups of the compound when in its ring form.

Preferably, each of the organic compound(s) is a natural ingredient, that is, it is obtained directly or indirectly from a natural product such as a plant-derived product.

The organic compound(s) preferably independently have at least 5 hydroxyl groups, or at least 6 hydroxyl groups, or at least 10 hydroxyl groups, or at least 15 hydroxyl groups, or at least 20 hydroxyl groups. In some embodiments, the organic compound(s) have at most 12 hydroxyl groups, or at most 10 hydroxyl groups. In some embodiments, one or more of the organic compound(s) is a polymeric polyol such as a glycogen. In other embodiments, one or more of the organic compound(s) is a small molecule comprising at most 20 carbon atoms, or at most 15 carbon atoms, or at most 10 carbon atoms. A mixture of any of the aforementioned compounds may be present.

Preferably the molecular weight of at least one or each of the organic compound(s) is at least 150, or at least 180. In some embodiments, the molecular weight of at least one or each of the organic compound(s) is at least 300. The molecular weight of each of the organic compound(s) is at most 10000. Preferably, the molecular weight of at least one or each of the organic compound(s) is at most 5000, or at most 2000, or at most 1000, or at most 500. In some embodiments, the molecular weight of at least one or each of the organic compound(s) is from 150 to 500, or from 150 to 200, or from 300 to 500. Generally, low molecular weight compounds are likely to give rise to a higher osmolality than high molecular weight compounds, whereas high molecular weight compounds may be liable to adversely affect viscosity. As such, the amount of polyhydric alcohol and/or sugar can be tuned to provide a low osmolality composition depending on its molecular weight. In embodiments where the maximum molecular weight of the organic compound(s) is 500, the lubricant preferably comprises a total of from 5 to 20 wt % by weight of the organic compound(s), preferably from 5 to 18 wt % or from 5 to 15 wt %. Surprisingly, it has been found that the lubricant has the desired effect on transparency even when the organic compound(s) are included in this amount. In embodiments where the organic compound(s) may have a higher molecular weight, they may be included in higher total amounts, such as from 15 to 25 wt %.

Preferably, one or more of the organic compound(s) has at least 2.5 hydroxyl groups per 100 molecular weight, more preferably at least 3.

Preferably, where the organic compound(s) comprise or consists of one or more polyhydric alcohols, the polyhydric alcohol(s) is or comprise a sugar alcohol. The term "sugar alcohol" is known in the art and refers to a polyhydric alcohol corresponding to a sugar in which the carbonyl group of the open chain form of the sugar is reduced to a hydroxyl group. Sugar alcohols are typically, although not necessarily, derived from sugars. A sugar alcohol may, for instance, be produced by reducing the carbonyl group of the open chain form of the corresponding sugar. However, some sugar alcohols are naturally occurring. The sugar alcohol(s) that may be used in the present invention are preferably naturally occurring and are preferably not produced by reducing the carbonyl group of the open chain form of the corresponding sugar. Suitable sugar alcohols for use in the present invention include sorbitol, maltitol, mannitol, xylitol, lactitol, isomalt and hydrogenated starch hydrolysates (HSH). In cases where the sugar alcohol includes a sugar moiety and that sugar moiety exists in equilibrium with an open chain form, references herein to the number of hydroxyl groups in the compound refers to the number of hydroxyl groups of the compound when in its ring form.

In some embodiments, the organic compound(s) are independently selected from the group consisting of a disaccharide and a sugar alcohol derived from a disaccharide. The disaccharide may, for instance, be sucrose, trehalose, lactose, or maltose. The sugar alcohol derived from a disaccharide may, for instance, be maltitol. By "derived from" it is meant that the sugar alcohol corresponds to the disaccharide in which the carbonyl group of the open chain form of the disaccharide is reduced to a hydroxyl group. However, it does not necessarily need to be produced from the disaccharide (it may, for instance, be naturally occurring). When the organic compound(s) are independently selected from the group consisting of a disaccharide and a sugar alcohol derived from a disaccharide, the lubricant preferably comprises a total amount of from 5 to 15 wt % of these organic compound(s) by weight of the lubricant, more preferably from 6 to 14 wt %, still more preferably from 8 to 14 wt %, and most preferably from 11 to 13 wt %.

In other embodiments, the organic compound(s) are independently selected from the group consisting of a monosaccharide and a sugar alcohol derived from a monosaccharide. The monosaccharide may, for instance, be glucose, galactose, ribose, deoxyribose, L-arabinose, fructose, sorbose, or xylose. The sugar alcohol derived from a monosaccharide may, for instance, be sorbitol. "Derived from" has a corresponding meaning to that given in relation to disaccharides above. When the organic compound(s) are independently selected from the group consisting of a monosaccharide and a sugar alcohol derived from a monosaccharide, the lubricant preferably comprises a total amount of from 5 to 12 wt % of these organic compound(s) by weight of the lubricant, more preferably from 6 to 10 wt % and most preferably from 6 to 8 wt %.

The organic compound(s) may consist of or comprise a mixture of one or more monosaccharide-derived sugar alcohols and one or more disaccharide-derived sugar alcohols.

Most preferably, the organic compound(s) is or comprise sorbitol and/or maltitol. When sorbitol is the only one of the specified organic compounds present, the lubricant preferably comprises from 5 to 12 wt % of sorbitol by weight of the lubricant, more preferably from 6 to wt % and most preferably from 6 to 8 wt %. When maltitol is the only one of the specified organic compounds present, the lubricant preferably comprises from 5 to 15 wt % maltitol by weight of the lubricant, more preferably from 6 to 14 wt %, still more preferably from 8 to 14 wt %, and most preferably from 11 to 13 wt %.

Preferably, the lubricant comprises at least 70 wt % water, more preferably at least 75 wt %, and most preferably at least 80 wt % by weight of the lubricant. In some embodiments, the lubricant comprises at most 90 wt % water, or at most 85 wt %. As a result of the inclusion of the polyhydric alcohol and/or sugar in the invention, high levels of water can be included in the lubricant without giving rise to whitening of the condom.

Preferably, the lubricant has an osmolality of less than 1200 mOsm/kg, less than 1100 mOsm/kg, less than 1000 mOsm/kg, or from 800 to 1000 mOsm/kg. The osmolality is preferably measured by a freezing point depression method. As explained above, the WHO has recommended that stand-alone personal lubricants (i.e. those not pre-provided on a condom) have osmolalities of less than 1200 mOsm/kg. The present inventors have found that the inclusion of the polyhydric alcohols and/or sugars in the invention in the aforementioned amounts has an advantageous anti-whitening effect on the condom without increasing the osmolality of the lubricant to undesirable levels.

Preferably, the lubricant does not comprise any polyhydric alcohols other than the polyhydric alcohol comprising at least 4 hydroxyl groups and having a molecular weight of at least 120. In embodiments where one or more polyhydric alcohols other than the polyhydric alcohols described above are present, they are preferably present in an amount of at most 5 wt %, more preferably at most 3 wt %, still more preferably at most 2 wt %, still more preferably at most 1 wt %, and most preferably at most 0.5 wt %. Preferably, the lubricant is free or substantially free from polyhydric alcohols other than the polyhydric alcohols described above. The other polyhydric alcohols (which can include, for instance, glycerol and propylene glycol) are generally undesirable in the lubricants of the present invention because they typically have little effect on the prevention of whitening of the condom during storage and/or increase the osmolality of the lubricant to an unfavourably high value.

In an embodiment, the lubricant contains less than 5 wt %, less than 4 wt %, less than 3 wt %, less than 2 wt %, less than 1 wt %, or essentially no glycerol, propylene glycol or PEG having a molecular weight of 600 or less. In an embodiment, the lubricant is free of glycerol, propylene glycol or PEG having a molecular weight or 600 or less.

Preferably, the lubricant has a pH of from 3.5 to 5.0. This is intended to match the pH of the vagina. It is to be understood that when we are referring to the pH of the lubricant, we are referring to the pH of the lubricant on the one or more surfaces of the condom in the sealed package. This can be determined by removing the condom from the packaging, extracting an aliquot of lubricant from the surface of the condom and measuring the pH of the aliquot (or pooled aliquots across multiple condoms from the same batch, if needed). The pH is preferably measured at a temperature of 25° C. Preferably, the pH is measured after the condom has been stored in the sealed package for at least 3 months, preferably at least 6 months.

The pH of the lubricant extracted from the condom in this way is not necessarily the same as the pH of the lubricant when it was first applied to the condom. This is because in the absence of a strong buffer in the lubricant, the pH of the lubricant will typically equilibrate with the pH of the condom over time. The pH of the condom will be typically higher than that of the lubricant as applied to the condom, particularly in embodiments in which the condom is coated with an alkaline finishing powder. As such, the pH of the lubricant as applied to the condom will typically increase over time until it reaches its equilibrium value.

In some embodiments, the lubricant comprises a buffering agent or acid to adjust the pH. Suitable buffering agents comprise a polybasic acid and a salt of the polybasic acid (for instance a sodium salt). In these embodiments, the buffering agent is present in an amount of from 0.1 to 10 wt % by weight of the lubricant, still more preferably from 1 to 10 wt %, still more preferably from 2 to 8 wt %, and most preferably from 3 to 7 wt %. Preferably, the buffering agent comprises a polybasic acid and a salt of the polybasic acid in a weight ratio of the polybasic acid to the salt of from 1:5 to 10:1, more preferably from 1:2 to 5:1, still more preferably from 1:1 to 3:1. Preferably, the buffering agent comprises citric acid and sodium citrate, more preferably in the aforementioned weight ratios. Suitable acids comprise weak acids and more preferable weak organic acids. The present inventors have found that citric acid is an effective acidifying agent which has no detrimental effect on the structural integrity of the condom to which the lubricant is applied.

In some embodiments, the lubricant comprises a preservative. In these embodiments, the preservative is preferably present in an amount of from 0.01 to 5 wt % by weight of the lubricant, more preferably from 0.05 to 2 wt %, still more preferably from 0.1 to 1 wt %. Preferably, the preservative is or comprises benzoic acid and/or a benzoic acid salt, preferably sodium benzoate or chlorphenesin. The present inventors have found that benzoic acid/salt thereof is an effective preservative for use in the lubricant of the present invention, particularly at the desired acidic pH. Preferably, the lubricant is free of parabens.

The lubricant of the invention further comprises a thickener. Suitable thickeners include a carbomer, a hydroxyethylcellulose, a xanthan gum, an alginate, an acrylate, a methacrylate, a silicone, a ceramide and a polyvinyl pyrrolidone, agar, locust bean gum and gum arabic.

Preferably, the thickener is cross-linked polyacrylic acid, hydroxyethylcellulose, or xanthan gum, more preferably xanthan gum. Where used, the thickener is preferably present in an amount of from 0.05 to 2 wt % by weight of the lubricant, more preferably from 0.01 to 2 wt %, still more preferably from 0.1 to 1 wt %. In an embodiment, the lubricant is free of dimethicone or free of any silicone.

In some embodiments, the lubricant comprises a moisturising agent, preferably in an amount of from 0.01 to 2 wt %, more preferably from 0.02 to 1 wt %, and most preferably from 0.05 to wt % by weight of the lubricant. Preferably the moisturising agent is or comprises hyaluronic acid, sodium hyaluronate and/or collagen.

In some embodiments, the lubricant comprises a surfactant. The surfactant may help the lubricant to migrate along the length of the condom during storage, in cases when the lubricant is dosed onto only a part of the condom surface during manufacturing. In some embodiments, the surfactant is present in an amount of at most 2 wt %, or at most 1 wt %, or at most 0.5 wt % by weight of the lubricant. In some embodiments, the surfactant is present in an amount of at least 0.05 wt %, or at least 0.1 wt % by weight of the lubricant.

It is preferred that the lubricant is free or substantially free from artificial colourants and/or flavourings. By substantially free it is meant that any artificial colourants and/or flavourings are present in a total amount of less than 1 wt % by weight of the lubricant, preferably less than 0.5 wt %, more preferably less than 0.1 wt %. In some embodiments, the lubricant may contain an odour masker, such as a composition which masks the bad smell of NRL.

Of course, the lubricant itself is preferably transparent. The anti-whitening effect of the lubricant on the condom is most readily observable when the lubricant itself is transparent.

Preferably, the aqueous lubricant comprises a solution of the specified organic compound(s), and any of the aforementioned optional components of the invention, in water. As such, all of the ingredients of the lubricant are preferably soluble in water, at least in the quantities in which they are used. The lubricant preferably does not comprise an oil. The lubricant is preferably not in the form of an emulsion.

Preferably, the lubricant has a viscosity of from 100 to 10,000 mPa·s, more preferably from 500 to 2000 mPa·s, still more preferably from 800 to 1000 mPa·s. The viscosity may be measured using a Brookfield viscometer, at a temperature of 20° C. and a shear rate of 50 rpm using spindle RV04.

In some embodiments, the condom comprises, on one or more surfaces thereof, a finishing powder. The one or more surfaces may be an inner surface and/or an outer surface of the condom. Preferably, the condom comprises the finishing powder on both an inner surface and an outer surface. Finishing powders are known in the art. They are typically alkaline, and are typically based on compounds such silica, talc, carbonates, cornstarch and the like. They are used to prevent the surfaces of the condom from sticking to each other, and to assist with donning. In particular, including a finishing powder on an inner surface serves to prevent the condom from sticking to itself, while including a finishing powder on an outer surface also serves to prevent the condom from sticking to other condoms during production.

In embodiments in which the condom comprises, on one or more surfaces thereof, a finishing powder, the finishing powder is preferably provided in an amount of at most 100 mg, preferably at most 50 mg, and most preferably from 20 to 40 mg. The use of an overly high amount of finishing powder tends to increase the opacity of the coated condom, which is undesirable in the context of the present invention. The low amounts of finishing powder described herein would make the whitening effect of many existing aqueous lubricants more noticeable, since the small amount of finishing powder itself would be having little effect on the opacity of the condom. As such, the advantageous anti-whitening properties of the lubricant of the present invention are particularly noticeable when the finishing powder is used in a low amount. In some embodiments, the condom does not comprise a finishing powder. In other embodiments, the condom comprises a finishing powder comprising carbonate (such as magnesium carbonate and/or calcium carbonate) and/or corn starch.

Preferably, the condom of the present invention, including the aqueous lubricant and optional finishing powder comprised on one or more surfaces thereof, is transparent. It is to be understood that the property of transparency in this context refers to the condom in an unrolled state, having been removed from the packaging, since a rolled portion of a rolled condom can appear to be substantially opaque, even if the condom material itself is transparent. Indeed, the packaging itself may be opaque. Preferably, the condom, including the aqueous lubricant and optional finishing powder comprised on one or more surfaces thereof, is transparent after storage in the sealed package for at least 6 months, or at least 12 months, or at least 18 months, or at least 24 months at a temperature of from 10 to 40° C. Preferably, the transparency of the condom, including the aqueous lubricant and optional finishing powder comprised on one or more surfaces thereof, after storage in the sealed package, is substantially the same as the transparency of the condom before the aqueous lubricant or any optional finishing powder are applied.

Preferably, the condom, including the aqueous lubricant and optional finishing powder comprised on one or more surfaces thereof, has a haze value of at most 70%, preferably after the storage periods specified in the immediately preceding paragraph. Preferably, the haze value is at most 60%, still more preferably at most 50%, still more preferably at most 40%, and most preferably at most 30%. In some embodiments, the haze value is at least 10%, or at least 15%. Haze value is defined herein elsewhere.

Preferably, the condom, including the aqueous lubricant and optional finishing powder comprised on one or more surfaces thereof, has a haze value that is at most 10% higher, in relative terms, than the haze value of the condom before the application of the lubricant and optional finishing powder, preferably after the storage periods specified above. In embodiments where the condom includes a finishing powder, the condom, including the aqueous lubricant and finishing powder comprised on one or more surfaces thereof, has a haze value that is at least 50% lower, at least 60% lower, or at least 70% lower, in relative terms, than the haze value of the condom after the finishing powder is applied but before the lubricant is applied. This is preferably the case after the storage periods specified above. That is, the application of the lubricant may increase the transparency of a condom coated with a finishing powder, and maintain this increase in transparency during storage.

In certain preferred embodiments, the present invention provides a packaged condom comprising:

a sealed package; and within the package, a natural rubber latex condom;

wherein the condom comprises, on one or more surfaces thereof, an aqueous lubricant;

wherein the aqueous lubricant comprises a thickener and from 5 to 19 wt % (preferably from 8 to 13 wt %), by weight of the lubricant, of a polyhydric alcohol, the polyhydric alcohol having at least 8 hydroxyl groups (preferably at least 9 hydroxyl groups) and a molecular weight of from 300 to 500; and wherein the aqueous lubricant comprises from 0 to 2 wt % of polyhydric alcohols other than the polyhydric alcohol having at least 8 (or preferably 9) hydroxyl groups and a molecular weight of from 300 to 500.

In these embodiments, the lubricant preferably comprises maltitol and the lubricant preferably has an osmolality of less than 1200 mOsm/kg and/or a pH of from 3.5 to 5.0.

In certain preferred embodiments, the present invention provides a packaged condom comprising:

a sealed package; and within the package, a natural rubber latex condom;

wherein the condom comprises, on one or more surfaces thereof, an aqueous lubricant; and wherein the aqueous lubricant comprises a thickener and from 5 to 19 wt % (preferably from 6 to 10 wt %), by weight of the lubricant, of a polyhydric alcohol, the polyhydric alcohol having at least 5 hydroxyl groups (preferably at least 6 hydroxyl groups) and a molecular weight of from 150 to 200; and wherein the aqueous lubricant comprises from 0 to 2 wt % of polyhydric alcohols other than the polyhydric alcohol having at least 5 (or at least 6) hydroxyl groups and a molecular weight of from 150 to 200.

In these embodiments, the lubricant preferably comprises sorbitol and the lubricant preferably has an osmolality of less than 1200 mOsm/kg and/or a pH of from 3.5 to 5.0.

According to a second aspect, the present invention provides a method for preparing a packaged condom. The method comprises the following steps:

(i) providing an aqueous lubricant, wherein the aqueous lubricant comprises a thickener and, in a total amount of from 5 to 25 wt % by weight of the lubricant, one or more organic compounds independently selected from the group consisting of a polyhydric alcohol and a sugar, each of said one or more organic compound(s) having at least 4 hydroxyl groups and a molecular weight of at least 120;

(ii) providing a condom as defined in the first aspect;

(iii) applying a dose of the aqueous lubricant to one or more surfaces of the condom to form a lubricated condom in which the lubricant is in contact with the natural rubber latex and/or synthetic polyisoprene; and (iv) sealing the lubricated condom within a package.

While these steps are intended to be carried out sequentially, there may be some overlap between the steps when the method is performed in a continuous manner, and additional steps may also be present, such as electrical testing of the condom for holes.

In the step of providing an aqueous lubricant, the aqueous lubricant is substantially the same as the lubricant as defined in relation to the first aspect. It will be appreciated, however, that the aqueous lubricant of the first aspect is the lubricant comprised on the one or more surfaces of the condom, whereas the aqueous lubricant in step (i) above refers to the lubricant before it is applied to the one or more surfaces of the condom. In step (i) above, the lubricant before application to the condom preferably has a pH of from 3.0 to 5.0, more preferably from 3.0 to 4.5, from 3.0 to 4.0 or from 3.5 to 4.5. As explained above, while the pH of the lubricant may increase as it equilibrates with the surface of the condom (including any finishing powder), this can be mitigated at least to some extent by the use of a suitable buffering system or acid.

In step (ii), the condom may be provided in a rolled state. In this embodiment, the dose of lubricant in step (iii) may be applied at or near a tip of the rolled condom. The lubricant may then migrate along the rolls of the condom over time (including after the condom is sealed within the package). In this embodiment, the condom may already be within the package, or on a material which will form a part of the package (such as one piece of foil), at the time the dose of lubricant is applied. Only the sealing step must necessarily take place after the lubricant is applied.

In an alternative embodiment, in step (ii), the condom is provided in an unrolled state. In this embodiment, the dose of lubricant in step (iii) is applied to one or more surfaces of the condom prior to rolling. The lubricant may be applied in a variety of known ways, for example, by spraying, rolling over a sponge soaked with the lubricant, or the dose of lubricant may be applied to one or more spots along a length of the condom prior to rolling. It will be appreciated that if the lubricant is pre-applied to the condom in all or substantially all of the area where it is required, such that it does not need to migrate to the desired area, a higher viscosity of the lubricant may be tolerated.

In some embodiments, the method further comprises a step of coating one or more surfaces of the condom with a finishing powder. The one or more surfaces may be an inner and/or an outer surface, preferably an inner surface and an outer surface. This is done prior to rolling, and before any lubricant is applied. The step of coating one or more surfaces of the condom with a finishing powder may comprise applying the finishing powder to the one or more surfaces as a powder or as a liquid slurry (preferably an aqueous slurry). In the latter embodiment, the water is allowed to evaporate to form the coating of the finishing powder on the one or more surfaces of the condom.

Preferably, the packaged condom prepared by the method of the second aspect is the packaged condom of the first aspect.

According to a third aspect, the present invention provides a packaged condom obtainable by or obtained by the method according to the second aspect.

According to a fourth aspect, the present invention provides the use of an aqueous lubricant as defined in the second aspect to lubricate one or more surfaces of a condom as defined in the first aspect, such that the lubricant is in contact with the natural rubber latex and/or synthetic polyisoprene, while maintaining the transparency of the condom during storage within a sealed package.

Preferably, the transparency is maintained for at least 6 months' storage, or at least 12 months' storage, or at least 18 months' storage, or at least 24 months' storage, at a temperature of from 10 to 40° C. The condom may comprise, on one or more surfaces thereof, a finishing powder, preferably in an amount of at most 100 mg, preferably at most mg, and most preferably from 20 to 40 mg.

After said storage, the condom, including the aqueous lubricant and optional finishing powder comprised on one or more surfaces thereof, preferably has a haze value that is less than 10% higher, in relative terms, than the haze value of the condom before the application of the lubricant and optional finishing powder. In embodiments where a finishing powder is included, the condom, including the aqueous lubricant and finishing powder comprised on one or more surfaces thereof, has a haze value that is at least 50% lower, at least 60% lower, or at least 70% lower, in relative terms, than the haze value of the condom after the finishing powder is applied but before the lubricant is applied.

The foregoing aspects may be freely combined with any of the foregoing aspects disclosed herein.

EXAMPLES

The present invention will now be described in relation to the following non-limiting Examples.

Example 1

Following an observation by the inventors that a commercially available natural rubber latex condom, lubricated with an aqueous lubricant, appeared white after 7 days' storage in a sealed package, whereas the same condom lubricated with silicone oil appeared transparent, the inventors sought to investigate whether water was causing or at least contributing to the whitening. To do this, a natural rubber latex condom was immersed in deionized water. Initially, the condom was observed to be transparent. After 5 hours, the condom appeared white. The longer the condom was immersed, the whiter it appeared. It was therefore concluded that the water in the existing aqueous lubricant was causing or at least contributing to the whitening of the condom.

Example 2

Solutions of different concentrations of polyhydric alcohols (glycerol, 1,3-propanediol, PEG400 and sorbitol) were tested for their effect on the whitening of a transparent natural rubber latex condom during storage. For each composition in Table 1, 600 mg of the solution was dosed onto the tip of a rolled transparent natural rubber latex condom. In each case, the solution was transparent prior to application to the condom, and the condom was found to be transparent immediately after application of the solution. The treated condom was then sealed in a foil package. After storage under the conditions shown in Table 1, the condom was removed from the packaging and inspected. The visual appearance of the condom is recorded in Table 1 (T=transparent, L=translucent, O=opaque).

TABLE 1

Testing of different polyhydric alcohols for effect on whitening of a transparent natural rubber latex condom

| Composition | A | B | C, D, E, F, G, H | I | J, K, L, M, N, O | P, Q, R, S, T | U | V | W | X |
|---|---|---|---|---|---|---|---|---|---|---|
| Water | 100 | 90 | balance | 90 | balance | balance | 20 | 0 | 95 | 90 |
| Glycerol | | 10 | 20, 40, 50, 60, 80, 100 | | | | | | | |
| 1,3-Propanediol | | | | 10 | 20, 40, 50, 60, 80, 100 | | | | | |
| PEG400 | | | | | | 10, 20, 40, 50, 60 | 80 | 100 | | |
| Sorbitol | | | | | | | | | 5 | 10 |
| Transparency of lubricated condom (after 7 days' storage at 70° C.)[#] | O | O | L | O | L | L | T | T | T | T |

[#]No further change was observed for any of the samples after 28 days' storage at 70° C.

As can be seen from Table 1, the transparency is not only affected by the water content of the applied solution, but also by the selection of the solute. As well as pure water, glycerol and 1,3-propanediol themselves caused whitening when used at 100% concentration; when in solution with water, they were found to have a very limited anti-whitening effect of the water. In particular, the condom was still found to be opaque after storage if 10 wt % glycerol or 10 wt % 1,3-propanediol was included. Including higher levels of glycerol or 1,3-propanediol (lower levels of water) prevented the condom from going fully opaque, but the condom appeared translucent and not transparent. PEG400 was able to maintain the transparent appearance of the condom but only when included at very high concentrations (at least 80 wt %).

Sorbitol was the only polyhydric alcohol tested that was able to keep the condom transparent at low concentrations (5 wt % or 10 wt %), or put another way, sorbitol in these solutions does not itself cause whitening and additionally enables a high concentration of water to be used.

Example 3

An aqueous lubricant formulation in accordance with the invention was prepared and dosed onto the tips of two rolled transparent natural rubber latex condoms (600 mg of lubricant per condom). The lubricated condoms were sealed in individual foil packages. After 1 week of storage at either room temperature or 70° C., the condoms were removed from the packaging and observed to be transparent. The lubricant composition is shown in Table 2.

TABLE 2

Lubricant in accordance with the invention

| | Composition 1 (wt %) |
|---|---|
| Water | 82.8 |
| 1,2-Hexanediol | 1 |
| Phenethyl Alcohol | 1 |
| Glycerol | 4 |
| Xanthan gum | 0.7 |
| Sodium hyaluronate | 0.1 |
| Lactic acid/Potassium Lactate | 0.4 |
| Sorbitol | 10 |

Example 4

The haze value (%) was measured for a series of natural rubber latex condoms based on ASTM Standard D 1003. The procedure involved the following steps:

the condom was removed from its packaging (when present), unrolled, and cut along the length of the condom from the open end to the closed end;

the cut condom was laid on a surface as a flat film;

three spots were marked on the film (a first spot at the end of the film that previously formed the closed end of the condom or as close thereto as possible, a second spot at the end of the film that previously formed the open end of the condom or as close thereto as possible, and a third sport at a midpoint between the first and second spots);

the marked film was placed into a thin film sample holder;

the sample holder was placed into a UV-Visible spectrophotometer (BYK Haze-gard i);

the haze value was measured at each of three spots (specifically for a circle having a diameter of 18 mm encompassing each of the three spots); and the haze value for the condom was calculated as the mean average of the three measurements (open end, closed end and midpoint).

The results are shown in Table 3.

TABLE 3

Measured haze values for a selection of lubricated condoms

| Condom | Finishing powder | Lubricant | Haze (open end) (%) | Haze (mid body) (%) | Haze (closed end) (%) | Haze (condom) (%) |
|---|---|---|---|---|---|---|
| CE1[#] | Carbonate-based | None | 84.28 | 87.50 | 83.31 | 85.03 |
| CE2[#] | Corn starch-based | None | 57.19 | 58.37 | 58.72 | 58.09 |
| CE3[##] | Carbonate-based | Silicone oil | 72.00 | 55.42 | 45.78 | 57.73 |
| CE4[##] | Corn starch-based | Silicone oil | 17.00 | 19.85 | 14.08 | 16.98 |

([#]after dipping; [##]removed from packaging)

It was noted that there was a direct association between the measured haze value and the observed transparency of the condoms: the most transparent condoms had the lowest haze values and vice versa. This validated the haze value as a parameter for quantifying the transparency of lubricated (and unlubricated) condoms.

Example 5

Several lubricants in accordance with the present invention were prepared. Their osmolalities were measured by a freezing point depression method. In particular, 100 µL of each test sample was pipetted into sample tubes, which were placed in the freezing chamber of a LOSER 0M819 Freezing Point Osmometer. The freezing point depressions were then determined by the osmometer and converted to osmolality values.

The pH values of the lubricants were measured using a pH probe at room temperature.

The viscosities of the lubricants were also measured at 20° C. and a shear rate of 50 rpm using a Brookfield viscometer, spindle RV04.

The compositions together with the measured properties are shown in Table 4.

TABLE 4

Exemplary lubricants in accordance with the invention

| | Composition | | | | |
|---|---|---|---|---|---|
| | 2 | 3 | 4 | 5 | 6 |
| Water | 85.3 | 86.3 | 80.3 | 81.3 | 83.3 |
| Xanthan Gum FNCS | 0.5 | 0.5 | 0.5 | 0.5 | 0.5 |
| Sodium hyaluronate | 0.1 | 0.1 | 0.1 | 0.1 | 0.1 |
| Citric acid | 3.5 | 3.5 | 3.5 | 3.5 | 3.5 |
| Sodium citrate | 2.4 | 2.4 | 2.4 | 2.4 | 2.4 |
| Benzoic acid | 0.2 | 0.2 | 0.2 | 0.2 | 0.2 |
| Sorbitol | 8 | 7 | N/A | N/A | N/A |
| Maltitol | N/A | N/A | 13 | 12 | 10 |
| pH | 3.56 | 3.56 | 3.56 | 3.57 | 3.59 |
| Viscosity/mPa · s | 840 | 840 | 840 | 900 | 860 |
| Osmolality/mOsm/kg | 1088 | 1005 | 1133 | 1099 | 941 |

All of the lubricants were found to have a low osmolality meeting the WHO recommendation of less than 1200 mOsm/kg.

The lubricants were each then dosed (600 mg) onto the tip of a rolled transparent natural rubber latex condom. The lubricated condoms were sealed in foil packages. After 1 week of storage at either room temperature or 70° C., the condoms were removed from the packaging and inspected. All of the lubricated condoms were observed to be transparent after storage and removal from the foil package.

Example 6

Several lubricants in accordance with the present invention were prepared where the polyhydric alcohol is maltitol. Citric acid was used to adjust the pH of the lubricant and chlorphenesin and 1,2-hexanediol were used as the preservative. The lubricants were applied to transparent natural rubber latex condoms to test for their effect on whitening of the condoms.

TABLE 5

Exemplary lubricant in accordance with the invention

| | Composition | |
|---|---|---|
| | 7 | 8 |
| Water | 84.69 | 85.67 |
| Citric acid | 0 | 0.07 |
| Chlorphenesin | 0.2 | 0.2 |
| 1,2-hexanediol | 1 | 1 |
| Xanthan gum | 0.6 | 0.6 |
| Hyaluronic acid | 0.1 | 0.1 |
| Maltitol | 13 | 13 |
| Flavouring | 0.01 | 0.01 |
| Lactic acid/potassium lactate | 0.4 | 0 |

The lubricants were each then dosed (600 mg) onto the tip of a rolled transparent natural rubber latex condom. The lubricated condoms were sealed in foil packages. After 1 week of storage at 70° C., the condoms were removed from the packaging and inspected. All of the lubricated condoms were observed to be transparent after storage and removal from the foil package. Further, the condoms were strength tested and found to comply with the ISO standards with zero teat breakages.

The wt % values given herein are based on the total weight of the lubricant unless otherwise stated.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

The invention claimed is:

1. A packaged condom comprising:
a sealed package; and
within the sealed package, a condom comprising natural rubber latex and/or synthetic polyisoprene;
wherein the condom further comprises an aqueous lubricant on one or more surfaces thereof, the aqueous lubricant in contact with the natural rubber latex and/or synthetic polyisoprene,
wherein the aqueous lubricant comprises:
a thickener; and
one or more organic compounds in a total amount of from 5 to 25% by weight of the aqueous lubricant, the one or more organic compounds independently selected from the group consisting of a polyhydric alcohol and a sugar, each of said one or more organic compounds having at least 4 hydroxyl groups and a molecular weight of from 180 to 10000.

2. The packaged condom according to claim 1, wherein the one or more organic compounds are independently selected from the group consisting of a monosaccharide, a disaccharide, a sugar alcohol derived from a monosaccharide, and a sugar alcohol derived from a disaccharide.

3. The packaged condom according to claim 2, wherein the one or more organic compounds are independently selected from the group consisting of a disaccharide and a sugar alcohol derived from a disaccharide, and the lubricant comprises a total amount of from 5 to 15 wt % of the organic compound(s).

4. The packaged condom according to claim 2, wherein the one or more organic compounds are independently selected from the group consisting of a monosaccharide and a sugar alcohol derived from a monosaccharide, and the lubricant comprises a total amount of from 5 to 12 wt % of the organic compound(s).

5. The packaged condom according to claim 2, wherein at least one of the one or more organic compounds is sorbitol and/or at least one of the one or more organic compounds is maltitol.

6. The packaged condom according to claim 1, wherein each of said one or more organic compounds has a molecular weight of from 180 to 1000.

7. The packaged condom according to claim 1, wherein the aqueous lubricant comprises a total amount of from 5 to 20 wt % of the one or more organic compounds.

8. The packaged condom according to claim 1, wherein the polyhydric alcohol is a sugar alcohol and/or the one or more organic compounds are independently a polyhydric alcohol.

9. The packaged condom according to claim 1, wherein the aqueous lubricant comprises at least 75 wt % water.

10. The packaged condom according to claim 1, wherein the aqueous lubricant has an osmolality of less than 1200 mOsm/kg.

11. The packaged condom according to claim 1, wherein the aqueous lubricant has a pH of from 3.5 to 5.0 before being applied to the condom.

12. The packaged condom according to claim 1, wherein the condom further comprises, on one or more surfaces thereof, a finishing powder, wherein the finishing powder is provided in an amount of at most 100 mg.

13. The packaged condom according to claim 1, wherein the condom is transparent.

14. The packaged condom according to claim 1, wherein the condom is a natural rubber latex condom.

15. The packaged condom according to claim 1, wherein the lubricant comprises less than 5 wt % of glycerol, propylene glycol, polyethylene glycol having a molecular weight of 600 or less, or any combination thereof.

16. The packaged condom according to claim 1, wherein the condom comprises from 100 mg to 1.5 g of the aqueous lubricant.

17. A method for preparing a packaged condom, the method comprising:

(i) providing an aqueous lubricant, wherein the aqueous lubricant comprises a thickener and, one or more organic compounds in a total amount of from 5 to 25% by weight of the aqueous lubricant, the one or more organic compounds independently selected from the group consisting of a polyhydric alcohol and a sugar, each of said one or more organic compounds having at least 4 hydroxyl groups and a molecular weight of from 180 to 10000;

(ii) providing a condom comprising natural rubber latex and/or synthetic polyisoprene;

(iii) applying a dose of the aqueous lubricant to one or more surfaces of the condom such that the aqueous lubricant is in contact with the natural rubber latex and/or synthetic polyisoprene; and (iv) sealing the condom within a package.

18. A packaged condom obtainable by or obtained by the method according to claim 17.

19. A method of using an aqueous lubricant to lubricate one or more surfaces of a condom comprising natural rubber latex and/or synthetic polyisoprene while maintaining a transparency of the condom during storage within a sealed package, the method comprising applying the aqueous lubricant to one or more surfaces of the condom such that the aqueous lubricant is in contact with the natural rubber latex and/or synthetic polyisoprene, wherein the aqueous lubricant comprises a thickener and, in a total amount of from 5 to 25% by weight of the aqueous lubricant, one or more organic compounds independently selected from the group consisting of a polyhydric alcohol and a sugar, wherein each of the one or more organic compounds has at least 4 hydroxyl groups and a molecular weight of from 180 to 10000.

* * * * *